United States Patent
Katou et al.

(10) Patent No.: US 7,217,038 B2
(45) Date of Patent: May 15, 2007

(54) FIXING STRUCTURE FOR ROLLING BEARING

(75) Inventors: Tomohiko Katou, Kuwana (JP); Yosuke Oya, Kuwana (JP)

(73) Assignee: NTN Corporation, Osaka (JP)

(*) Notice: Subject to any disclaimer, the term of this patent is extended or adjusted under 35 U.S.C. 154(b) by 148 days.

(21) Appl. No.: 11/083,076

(22) Filed: Mar. 18, 2005

(65) Prior Publication Data

US 2005/0220382 A1 Oct. 6, 2005

(30) Foreign Application Priority Data

Mar. 23, 2004 (JP) ............................... 2004-084949

(51) Int. Cl.
*F16C 19/52* (2006.01)
(52) U.S. Cl. ...................................... 384/542; 384/445
(58) Field of Classification Search ................ 384/445, 384/537, 542
See application file for complete search history.

(56) References Cited

U.S. PATENT DOCUMENTS

| | | | | |
|---|---|---|---|---|
| 4,557,679 A | * | 12/1985 | Mori et al. | ............... 418/201.1 |
| 6,283,637 B1 | * | 9/2001 | Schnur et al. | ............... 384/519 |
| 6,409,390 B1 | * | 6/2002 | Bouzakis et al. | ........... 384/517 |
| 6,464,397 B2 | * | 10/2002 | Kobayashi | .................. 384/450 |
| 6,676,297 B1 | * | 1/2004 | Miyagawa et al. | ......... 384/450 |

\* cited by examiner

*Primary Examiner*—Thomas R. Hannon
(74) *Attorney, Agent, or Firm*—Arent Fox LLP

(57) ABSTRACT

In a fixing structure for a rolling bearing in which a bearing fixing ring is incorporated in a device and a rotating member is fixed to a bearing rotating ring using bolts, fastening areas with the bolts are set so that the natural frequency of the device as a whole is larger than the frequency of vibration resulting from the rotation of the rolling bearing. This prevents generation of noise or vibration in the rolling bearing.

5 Claims, 8 Drawing Sheets

FIXING STRUCTURE FOR ROLLING BEARING

BACKGROUND OF THE INTENTION a. Field of the Invention

The invention relates to a fixing structure for an ultra thin rolling bearing for use, for example, in an industrial robot, a machine tool, and medical equipment.

b. Related Art

A gantry bearing in a CT scanner is used as a rotating body bearing provided with an X-ray tube and photographing equipment typically used for image processing. The bearing is an ultra large size device having a bearing outer size of about 1 m and therefore typically coupled to the main body frame of the CT scanner using bolts when it is fixed to the frame.

FIG. 9 shows an example of the CT scanner used as a kind of medical equipment. As shown, in the CT scanner, X-rays generated by an X-ray tube device 50 are directed upon a subject 56 through a wedge filter 52 that equalizes the intensity distribution and a slit 54 that limits the intensity distribution. The X-rays passed through the subject 56 are received at a detector 58 and converted into an electrical signal for transmission to a computer that is not shown. The elements such as the X-ray tube device 50, the wedge filter 52, the slit 54, and the detector 58 are mounted to a rotating base 64 in a substantially cylindrical shape rotatably supported at a fixed base 62 via a bearing 60, and rotated around the subject 56 as the rotating base 64 rotates. In the CT scanner device, the X-ray tube device 50 and the detector 58 opposing each other rotate around the subject 56, so that projection data covering every angle in every aspect in a plane of the subject 56 for examination is obtained, and a tomogram is obtained based on the data using a preprogrammed restructuring program.

The rotating base 64 of the device is coupled to the width side of the rotating ring (hereinafter referred to as "bearing rotating ring") among the inner and outer rotating rings of the bearing 60. The dominant frequency for vibration resulting from the rotation of the bearing 60 is determined based on the number of bolts or the number of areas fastened with the bolts and the number of revolutions of the bearing 60. Meanwhile, the frame 62 fixed to the non-rotating ring (hereinafter referred to as "bearing fixed ring") among the inner and outer rings of the bearing 60 tends to have a relatively low natural frequency because the rigidity of the structure is reduced to satisfy a need for a more compact and simple device. Therefore, the frequency of vibration resulting from the rotation of the bearing 60 matches the natural frequency of the structure, and resonance is caused.

SUMMARY OF THE INVENTION

It is therefore a main object of the invention to reduce or prevent the resonance when the rolling bearing rotates.

The dominant frequency for vibration or associated noise occurs corresponding to a bolt number order component in the rotating speed (number of revolutions) of the bearing. So-called multi-angular distortion corresponding to the number of the fixing bolts is generated. When, for example, the bearing is fixed in seven positions, a septenary component in the rotating frequency is excited. The frequency determined based on the number of revolutions and the bolt number order component must not coincide with the natural frequency of the structure in order to reduce the resonance.

According to the invention based on this finding, the rotating member is fixed using bolts (or areas fastened with the bolts) whose number does not cause resonance with the natural frequency of the structure. More specifically, according to the invention, in a fixing structure for a rolling bearing in which a bearing fixing ring is incorporated in a device and a rotating member is fixed to a bearing rotating ring using bolts, fastening areas with the bolts are set so that the natural frequency of the device as a whole is larger than the frequency of vibration resulting from the rotation of the rolling bearing.

As a gantry bearing in a CT scanner, an ultra thin rolling bearing includes: an outer member having a raceway at an inner circumference thereof; an inner member having a raceway at an outer circumference thereof; a plurality of rolling elements interposed between the raceways of the inner and outer members; and a cage holding the rolling elements at prescribed intervals. One of the outer member and the inner member is fixed to a rotating base of the CT scanner rotating around a subject, and the other is fixed to a fixed base of the CT scanner. In this way, the rotating base of the CT scanner is supported rotatably to the fixed base.

According to the invention, the dominant frequency band changes and resonance is reduced.

FIG. 1 is a diagram for use in illustration of the basic concept of the invention. When the natural frequency of the structure such as a frame is 11.5 Hz, and the number of revolutions of the bearing is 180 rpm at maximum, the bearing rotating ring and the rotating member holding a heavy subject are connected with bolts in three positions in the circumferential direction, so that the peak frequency of the vibration resulting from the rotation of the bearing is not more than the natural frequency of the structure such as the frame, and resonance can be prevented. More specifically, in the example in FIG. 1, the peak frequencies of 60 rpm, 120 rpm, and 180 rpm are shown as an example. If the number of fastening areas with the bolts are three, the peak frequency of vibration resulting from the rotation of the bearing and the natural frequency of the structure do not match in any of these three regions of 60 rpm to 180 rpm. Therefore, the resonance can be reduced.

Now, an embodiment of the invention will be described in conjunction with the accompanying drawings.

DESCRIPTION OF THE PREFERRED EMBODIMENTS

Figure 1:
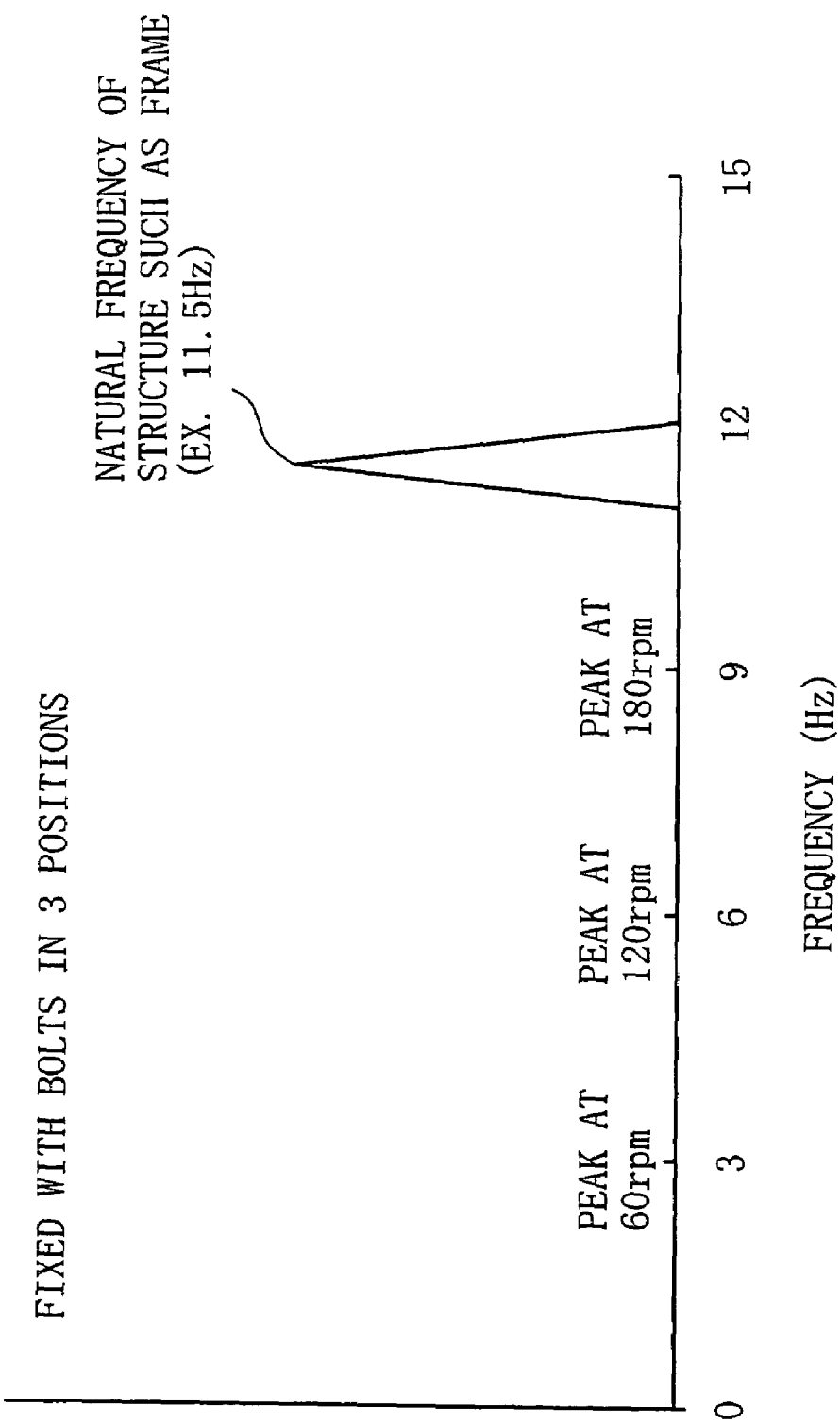
FIG. 1 is a graph for use in illustration of an embodiment of the invention.
Figure 2:
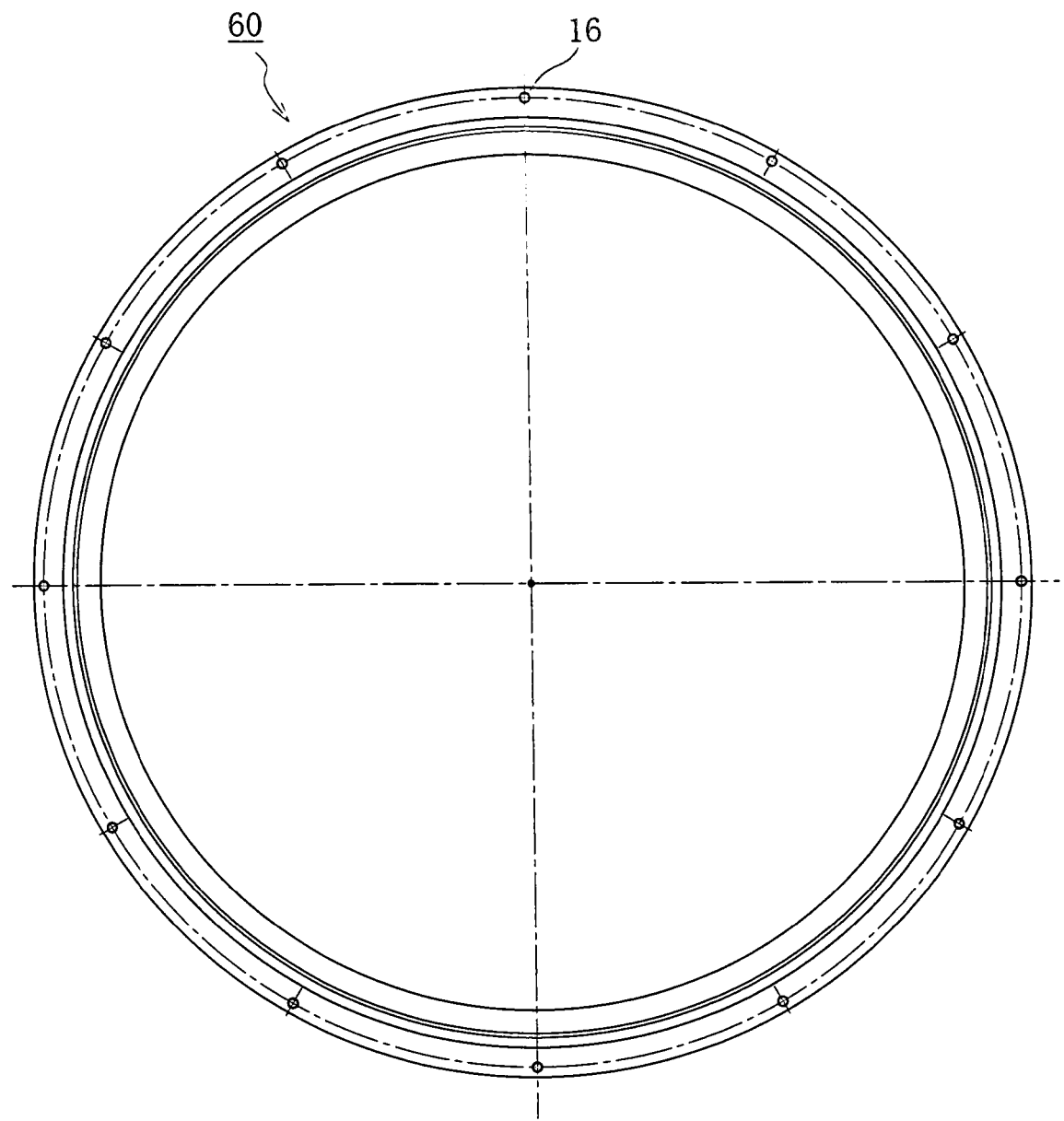
FIG. 2 is a front view of a rolling bearing.
Figure 3:
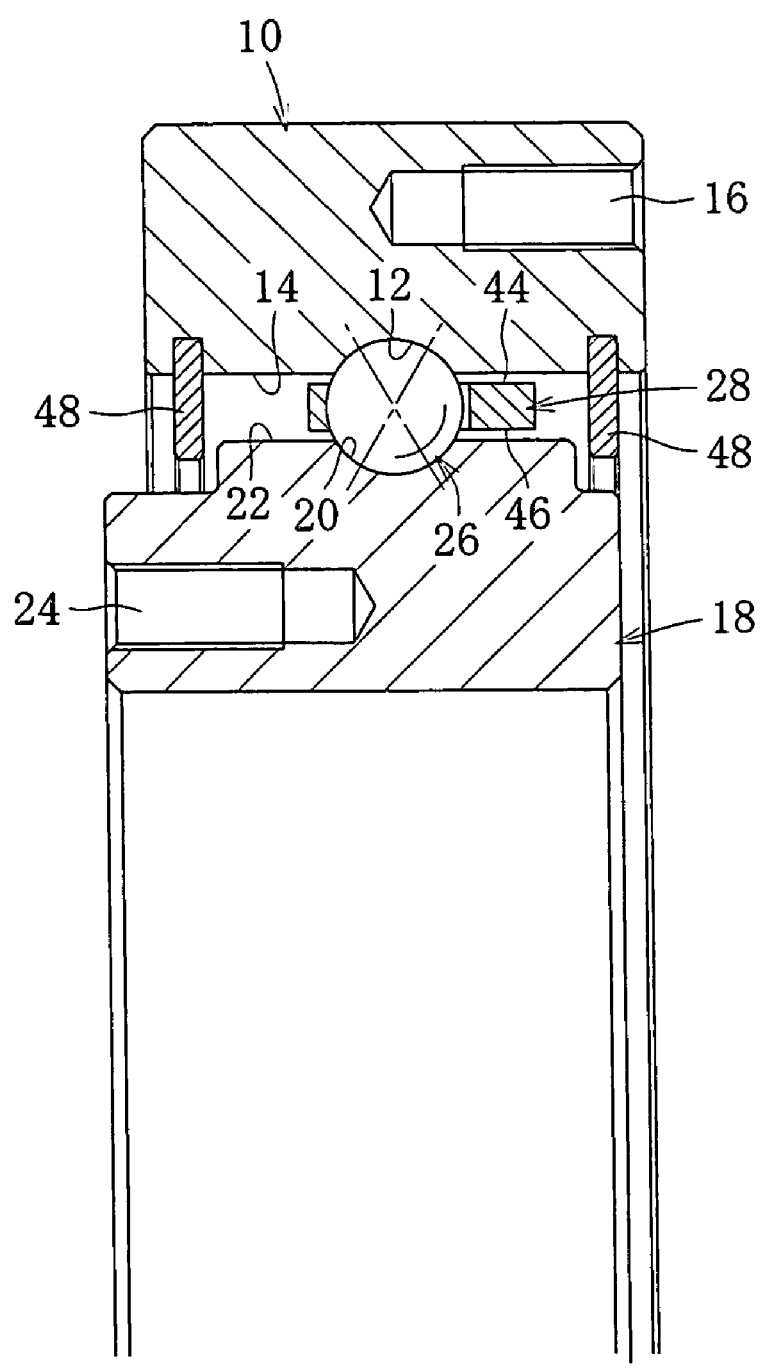
FIG. 3 is an enlarged sectional view of a rolling bearing.

Now, an ultra thin rolling bearing shown in FIGS. 2 and 3 will be described. In this example, FIG. 3 corresponds to a sectional view of the bearing 60 for use in the CT scanner in FIG. 9. The bearing 60 includes an outer member 10, an inner member 18, rolling elements 26, and a cage 28 as essential elements. The outer member 10 is in a ring shape and has a single raceway 12 at its inner circumference. The inner member 18 is in a ring shape and provided concentrically at the inner circumferential side of the outer member 10 and has a single raceway 20 at its outer circumference. A plurality of rolling elements 26 are interposed in a single row between the raceways 12 and 20 of the outer and inner members 10 and 18. The cage 28 holds the rolling elements 26 at prescribed intervals in the circumferential direction. The balls are shown as the rolling elements 26 by way of illustration, but rollers may be used instead. The reference numeral 48 refers to a seal device that seals each of the openings at both ends of the bearing in a non-contact state.

The bearing 60 is an ultra thin bearing and the value $\phi$ of the ratio $D_B$/PCD is not more than 0.03 ($\phi \leq 0.03$) in which $D_B$ represents the diameter of the ball 26 and PCD represents the pitch circle diameter. This is normally applied to a large size bearing whose PCD is about in the range from 500 mm to 1500 mm. More specifically, when the ball size is ½ inches (12.7 mm) and PCD is 1041.4 mm, $\phi$ is 0.012.

Figure 4:
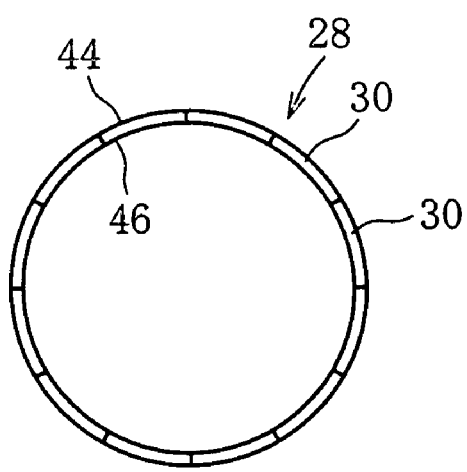
FIG. 4 is a front view of a cage.
Figure 5:
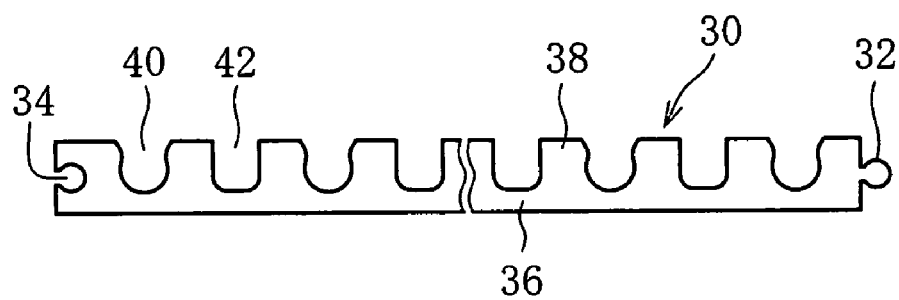
FIG. 5 is a development plan view of a segment forming a cage.

The cage 28 is made of a resin material unlike a conventional metal material. As shown in FIG. 4, the resin cage 28 is a split type having a plurality of resin segments 30 having a circular sectional shape connected in the circumferential direction to be in an annular form. As shown in FIG. 5, a raised fitting portion 32 and a recessed fitting portion 34 are formed on the ends of each of the segments 30. The recessed fitting portion 34 and the raised fitting portion 32 at ends of corresponding segments 30 are coupled with each other to couple the segments with each other, so that the annular cage 28 is formed. The segments 30 as shown each include a circular base portion 36 produced by dividing an annular member in a plurality of positions in the circumferential direction, pillar portions 38 extending in one direction in the axial direction from the base portion 36, and a plurality of pockets 40 and 42 provided between adjacent pillar portions 38.

The pockets 40 and 42 as shown are in different shapes. More specifically, the first pockets 40 have a retaining function for the ball 26 (including the capability of providing the balls at equal intervals) and the second pockets 42 have only the capability of providing the balls at equal intervals. The cage 28 according to the embodiment has these two kinds of pockets 40 and 42 alternately provided at equal intervals in the circumferential direction. The shapes or structures of the pockets 40 and 42 are only by way of illustration, and the pockets may have, for example, a single shape. In other words, pockets having various shapes and structures may be employed depending on the conditions of how the bearing is used.

There is a clearance (pocket clearance) between the surface of the ball 26 and the pocket inner surfaces in the first and second pockets 40 and 42. While the bearing rotates, the presence of the pocket clearance allows the cage 28 to move in the radial direction relatively to the ball 26. The relative movement causes the cage 28 to contact one of the outer circumferential surface 22 of the inner member 18 or the inner circumferential surface 14 of the outer member 10, so that the cage 28 is guided to rotate. In the shown embodiment, the outer circumferential surface 44 of the cage 28 is in contact with the inner circumferential surface 14 of the outer member 10, and in this case, the cage 28 is driven by the driving force from the outer member 10 to rotate as it contacts the outer member 10. Note that the inner circumferential surface 46 of the cage 28 may be contacted to the outer circumferential surface 22 of the inner member 18 to guide the cage 28 to rotate.

Figure 9:
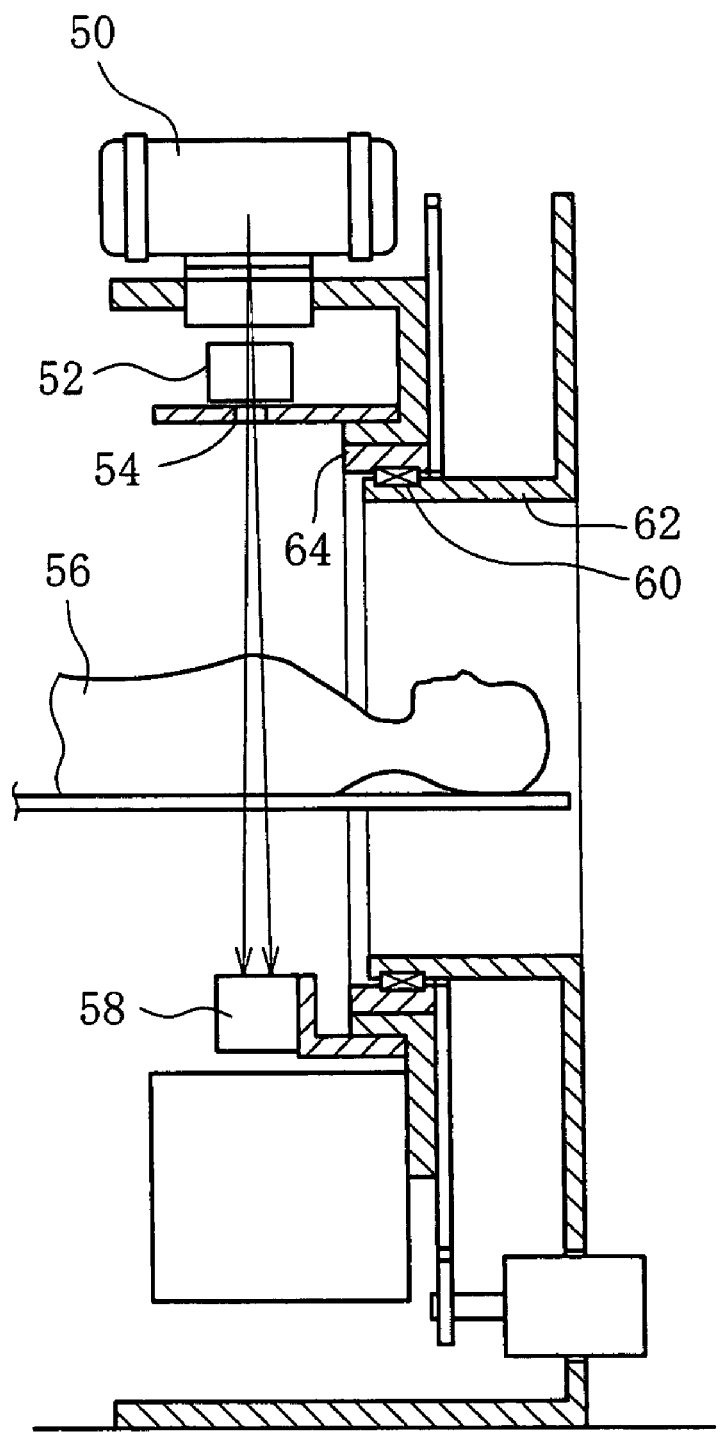
FIG. 9 is a sectional view of a CT scanner.

A screw hole 16 is formed on an end surface at one end (right side in FIG. 3) of the outer member 10, and fastening means such as a bolt (not shown) is screwed in the screw hole 16, so that the outer member 10 is fixed to the rotating base 64 of the CT scanner (see FIG. 9). A screw hole 24 is similarly formed on an end surface at the other end of the inner member 18, and fastening means such as a bolt (not shown) is screwed in the screw hole 24, so that the inner member 18 is fixed to the fixed base 62 (see FIG. 9). In this case, the outer member 10 serves as a rotating member that rotates together with the rotating base 64, and the inner member 18 serves as a non-rotating fixed member. Depending on the structure of the CT scanner, the outer member 10 may serve as the fixed side and the inner member 18 may serve as the rotating side that rotates together with the rotating base 64. As shown in FIG. 2, the screw holes 16 are provided at equal intervals in the circumferential direction of the outer member 10, and the screw holes 24 are provided at equal intervals in the circumferential direction of the inner member 18. The fastening areas by the bolts are normally provided at equal intervals in the circumferential direction, and the number of bolts in each fastening area may be more than one, though an example with one bolt will be described for the ease of illustration. The structure of the CT scanner has low rigidity to reduce the weight of the scanner, and therefore its natural frequency is low. A peak frequency of vibration is generated when the gantry bearing in the CT scanner rotates. When the natural frequency of the structure and the peak frequency caused by the rotation are near, resonance is caused, which gives rise to noise or vibration. While the resonance could be prevented by changing the rigidity of the structure to change the natural frequency or by changing the number of revolutions of the bearing if possible, the number of bolts for fixing to the bearing rotating ring is changed in this example to prevent the resonance.

Figure 6A:
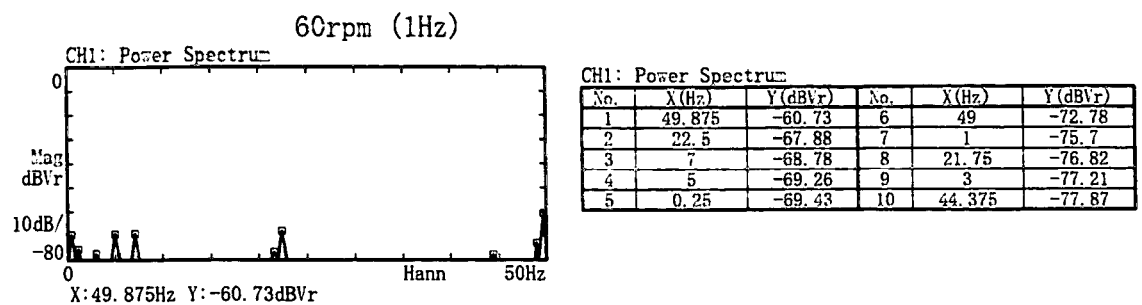
FIGS. 6A to 6C are power spectra when fixing is carried out in seven positions with bolts.
Figure 6B:
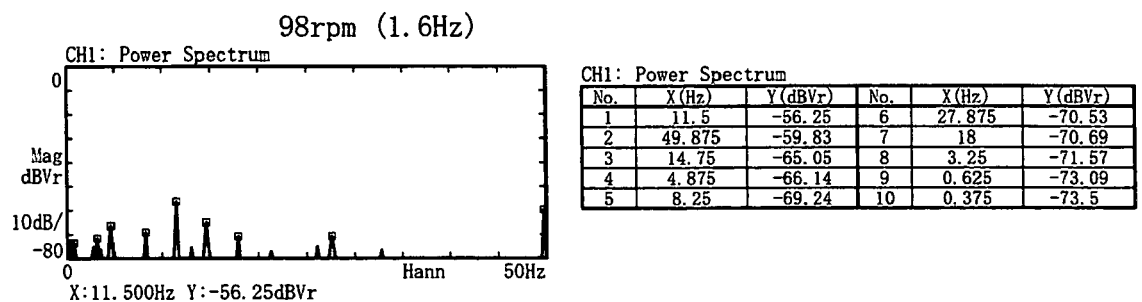
Figure 7A:
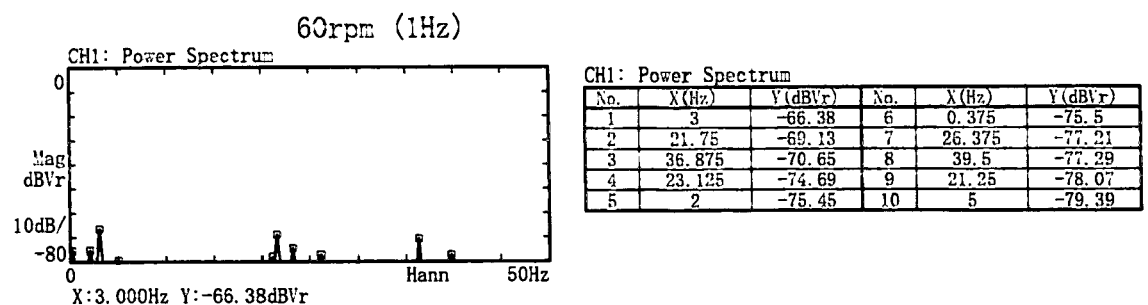
FIGS. 7A to 7C are power spectra when fixing is carried out in three positions with bolts.
Figure 7B:
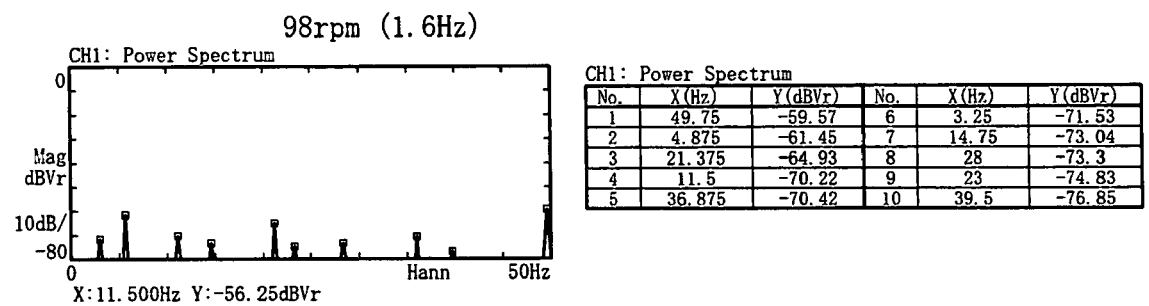
Figure 7C:
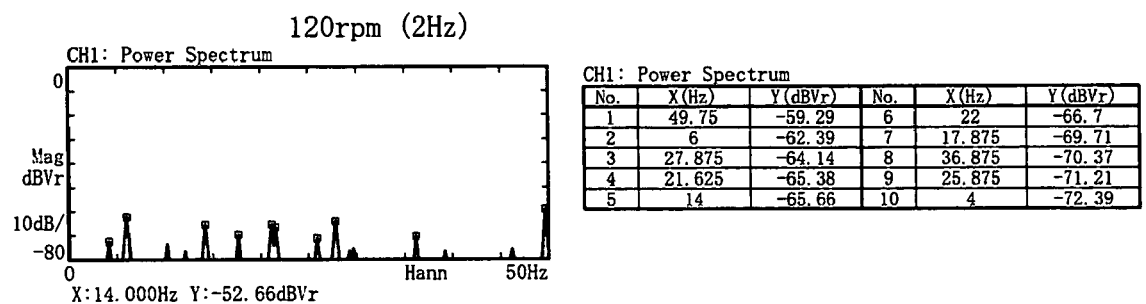
Figure 8A:
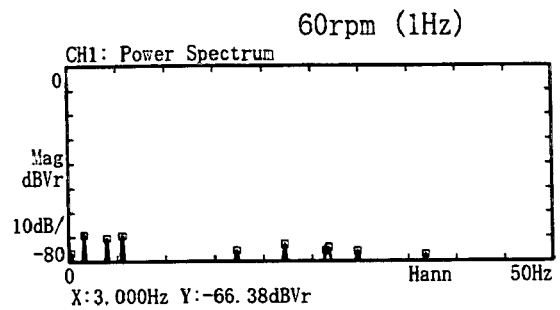
FIGS. 8A to 8C are power spectra when fixing is carried out in two positions with bolts.
Figure 8B:
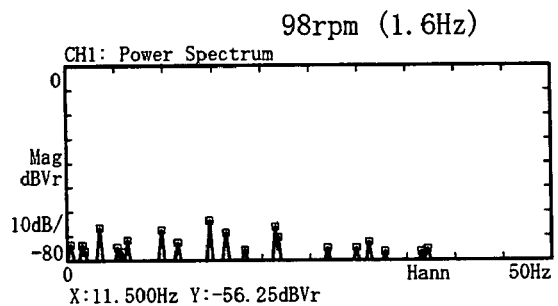
Figure 8C:
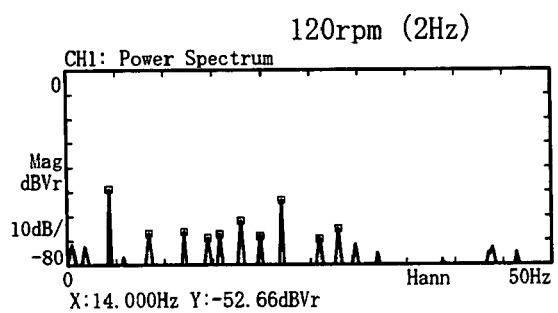

When, for example, the number of bolts is seven, and the number of revolutions of the bearing is 98 rpm (1.6 Hz), the vibration component is produced as 1.6 Hz×7=11.2≈11.5 Hz, which is maximum (see FIG. 6B). In this case, when the number of revolutions is 98 rpm (about 100 rpm) and the natural frequency of the structure such as the frame is, for example, 11.5 Hz, the natural frequency of the structure and the vibration component of the bearing are equal, and resonance is generated. When, for example, the number of bolts is changed to three, the vibration component of the bearing is produced as 1.6 Hz (98 rpm)×3=4.8 Hz≈4.9 Hz (see FIG. 7B), which is shifted from the natural frequency of the structure. Therefore, resonance is not generated.

Figure 6C:
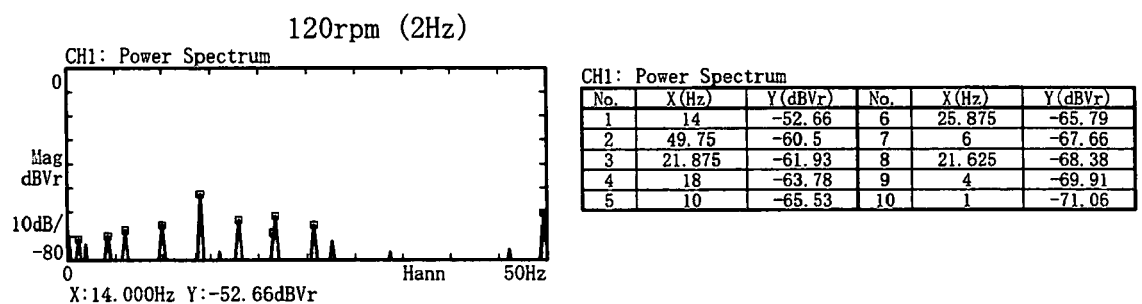

Herein, FIGS. 6A to 6C, FIGS. 7A to 7C, and FIGS. 8A to 8C each show a power spectrum or the root mean square of temporal or spatial fluctuation as a distribution of frequency components. The abscissa represents the frequency (Hz), and the ordinate represents the noise level (dB). In FIGS. 6A to 6C, the bearing is fixed in seven positions in the circumference. Similarly in FIGS. 7A to 7C, the bearing is fixed in three positions, and in FIG. 8A to 8C, in two positions. The number of revolutions is 60 rpm (1 Hz) in FIGS. 6A, 7A, and 8A, 98 rpm (1.6 Hz) in FIGS. 6B, 7B, and 8B, and 120 rpm (2 Hz) in FIGS. 6C, 7C, and 8C.

As in the foregoing, in the bearing fixed to the structure in the fastening areas provided at equal intervals on the circumference, the number of bolts is increased or reduced by at least one so that the number of bolts is not approximated to the value produced by dividing the natural frequency of the structure by the number of revolutions.

What is claimed is:

1. A fixing structure for a rolling bearing in which a bearing fixing ring is incorporated in a device and a rotating member is fixed to a bearing rotating ring using bolts, wherein the bolts are set in fastening areas at equal intervals in a circumferential direction so that the natural frequency of the device as a whole is larger than the frequency of vibration resulting from the rotation of the rolling bearing.

2. The fixing structure for a rolling bearing according to claim 1, wherein the rolling bearing is a gantry bearing in a CT scanner.

3. The fixing structure for a rolling bearing according to claim 2, wherein the rolling bearing is an ultra thin rolling bearing comprising:

an outer member having a raceway at an inner circumference thereof;

an inner member having a raceway at an outer circumference thereof;

a plurality of rolling elements interposed between the raceways of the inner and outer members; and a cage holding the rolling elements at prescribed intervals.

4. The fixing structure for a rolling bearing according to claim 3, wherein one of the outer member and the inner member is fixed to a rotating base of the CT scanner rotating around a subject, and the other thereof is fixed to a fixed base of the CT scanner.

5. The fixing structure for a rolling bearing according to claim 1, wherein the number of bolts in each fastening area is more than one.

* * * * *